(12) United States Patent
Pianowski et al.

(10) Patent No.: US 9,333,206 B2
(45) Date of Patent: May 10, 2016

(54) METHOD FOR TREATING FATIGUE

(76) Inventors: Luiz Francisco Pianowski, Bragança Paulista (BR); João Batista Calixto, Florianópolis (BR); Auro Del Giglio, São Paulo (BR)

( * ) Notice: Subject to any disclaimer, the term of this patent is extended or adjusted under 35 U.S.C. 154(b) by 38 days.

(21) Appl. No.: 14/009,102

(22) PCT Filed: Mar. 30, 2012

(86) PCT No.: PCT/BR2012/000092
§ 371 (c)(1),
(2), (4) Date: Sep. 30, 2013

(87) PCT Pub. No.: WO2012/129629
PCT Pub. Date: Oct. 4, 2012

(65) Prior Publication Data
US 2014/0073655 A1 Mar. 13, 2014

(30) Foreign Application Priority Data
Mar. 31, 2011 (BR) ...................................... 1101146

(51) Int. Cl.
*A61K 31/522* (2006.01)
*A61K 36/77* (2006.01)

(52) U.S. Cl.
CPC ............... *A61K 31/522* (2013.01); *A61K 36/77* (2013.01); *A61K 2236/00* (2013.01)

(58) Field of Classification Search
CPC .................................................... A61K 31/522
See application file for complete search history.

(56) References Cited

U.S. PATENT DOCUMENTS

| 5,502,056 | A | * | 3/1996 | Breitbarth ................. 514/263.31 |
| 2005/0089584 | A1 | * | 4/2005 | Gow et al. ..................... 424/727 |
| 2005/0202104 | A1 | | 9/2005 | Gianesello et al. |

FOREIGN PATENT DOCUMENTS

| FR | 2 687 548 | 8/1993 |
| FR | 2 712 191 | 5/1995 |
| JP | 2002-029981 | 1/2002 |
| JP | 2008-050331 | 3/2008 |
| WO | WO 97/42957 | 11/1997 |

OTHER PUBLICATIONS

Campos MR, Riechelmann R, Martins LC, Hassan BJ, Casa FB, Del Giglio A. Effect of guarana (Paullinia cupana) on fatigue in breast cancer patients undergoing systemic chemotherapy. J Clin Oncol. May 2010; 28(Suppl).*
Kennedy DO, Haskell CF, Wesnes KA, Scholey AB. Improved cognitive performance in human volunteers following administration of guarana (Paullinia cupana) extract: comparison and interaction with Panax ginseng. Pharmacol Biochem Behav. Nov. 2004;79(3):401-11.*
Weckerle CS, Stutz MA, Baumann TW. Purine alkaloids in Paullinia. Phytochemistry. Oct. 2003;64(3):735-42.*
de Oliveira Campos MP, Riechelmann R, Martins LC, Hassan BJ, Casa FB, Del Giglio A. uarana (Paullinia cupana) improves fatigue in breast cancer patients undergoing systemic chemotherapy. J Altern Complement Med. Jun. 2011;17(6):505-12. Epub May 25, 2011.*
Stasi R, Abriani L, Beccaglia P, Terzoli E, Amadori S. Cancer-related fatigue: evolving concepts in evaluation and treatment. Cancer. Nov. 1, 2003;98(9):1786-801.*
International Search Report for PCT/BR2012/000092, dated Jul. 16, 2012.
Supplementary International Search Report for PCT/BR2012/000092, dated Jul. 16, 2012.
Kennedy, et al., "Improved Cognitive Performance and Mental Fatigue Following a Multi-Vitamin and Mineral Supplement with Added Guaraná (*Paullinia cupana*)", 2008, Appetite 50, pp. 506-513.
Miranda VC, et al., "Effectiveness of Guaraná (*Paullinia cupana*) for Postradiation Fatigue and Depression: Results of a Pilot Double-Blind Randomized Study", The Journal of Alternative and Complementary Medicine, 2009, vol. 15, No. 4, pp. 431-433.

* cited by examiner

*Primary Examiner* — Paul Zarek
(74) *Attorney, Agent, or Firm* — B. Aaron Schulman, Esq.; Stites & Harbison, PLLC.

(57) ABSTRACT

The present invention refers to an active moiety of *Paullinia cupana* with enhanced activity against fatigue. Particularly related to cancers, and its manufacturing process, pharmaceutical compositions and drugs containing the same. Another object of the present invention is a method for treating fatigue, particularly related to cancers.

1 Claim, 5 Drawing Sheets

US 9,333,206 B2

METHOD FOR TREATING FATIGUE

FIELD OF THE INVENTION

The present invention refers to an active moiety of *Paullinia cupana* with enhanced activity against fatigue, particularly related to cancers, and its manufacturing process, pharmaceutical compositions and drugs containing the same. Another object of the present invention is a method for treating fatigue, particularly related to cancers.

BACKGROUND OF THE INVENTION

Cancer encompasses a set of diseases having, in common, a disordered growth of cells that invade tissues and organs, and may spread to other regions of the body (metastasis). It is estimated that the number of individuals showing cancer manifestations will increase up to 55% until 2020 (Warren J L et al.: Current and Future Utilization of Services From Medical Oncologists, J Clin Oncol.; 26: 3242-3247, 2008).

The survival increase has turned cancer into a chronic disease, and subjected cancer patients to greater suffering. Suffering is caused by the tumor, other symptoms related to the disease, health damage caused by the treatment and emotional charge involving the diagnosis.

Among the most common symptoms, fatigue, pain, dyspnea, cognitive changes, loss of appetite, cachexia, nausea or depression can be cited.

Fatigue is particularly pointed out by patients with cancer as one of the most frequent symptoms present in all stages of the disease, as well as the prevailing and most debilitating symptom in people with advanced stage of cancer. Studies showed that approximately 40 to 80% of patients report fatigue during and after the treatment of disease (Hofman et al.: Cancer-related fatigue: the scale of the problem. *Oncologist*. 12 Suppl 1:4-10, 2007).

Mota et al. teaches that fatigue can be considered a subjective syndrome with multiple causes, whose onset and expression involve physical and psychic aspects (Mota et al.: *Fadiga em pacientes com câncer avançado: conceito, avaliação e intervenção, Revista Brasileira de Cancerologia*—Volume 48 n°4, 2002).

The word fatigue is also commonly used to describe a set of illnesses, from a generic state of lethargy to a specific heat sensation in the muscles caused by hardworking. Physiologically, this represents a decrease in overall capacity, which can be dangerous when tasks that require constant concentration carried out, such as driving a vehicle, since when a person is sufficiently fatigued, short periods of sleepiness may be experienced (concentration loss).

It is reported that the fatigue sensation originates in the reticular activating system at the base of the brain. Musculoskeletal structures would have co-evolved with appropriate brain structures so that the entire set works constructively and adaptively (Edelman, G. M. *The remembered present: a biological theory of consciousness*. Nova York: Basic Books, 1989).

However, despite of being frequent and debilitating, fatigue can be considered the symptom to which less effective interventions are known, especially when compared to those indicated for the control of other symptoms, like pain.

Thus, although the forms of fatigue control currently available include the use of pharmacological and non-pharmacological therapies, its management still represents a challenge (Giglio et al.: *Fadiga relacionada ao câncer*, Algoritmos, Einstein: Educ Contin Saúde. 2010;8(1 Pt 2): 44).

Accordingly, alternative therapies, with energy products, have been proposed. For example, guarana (*Paullinia cupana*), an Amazon shrub, is widely used in the manufacture of syrups, tablets, powders and soft drinks, and it is responsible, among others, for the stimulant effect able to increase resistance in mental and muscular efforts, reduce muscle and mental fatigue, especially in people without cancer. This ability is related to the presence of high dose of caffeine—about 2.5 to 5% (Weckerle et al.: *Purine alkaloids in Paullinia*. Phytochemistry. 2003;64(3):735-42.)

However, although the powder obtained from *Paullinia cupana* fruit is usually recommended, as a stimulant, for patients suffering from cancer, studies conducted with 75 mg in patients with cancer did not result in positive effects against fatigue (Miranda et. al: *Guarana (Paullinia cupana) for chemotherapy-related fatigue, Study carried out at Serviço de Quimioterapia of Hospital Estadual Mário Covas—Santo André (SP)*, Brazil, Einstein. 2008; 6(2):195-9.)

Thus, there remains the need for an effective alternative for the treatment of fatigue, particularly fatigue related to cancer.

DESCRIPTION OF THE INVENTION

Figure 1A:
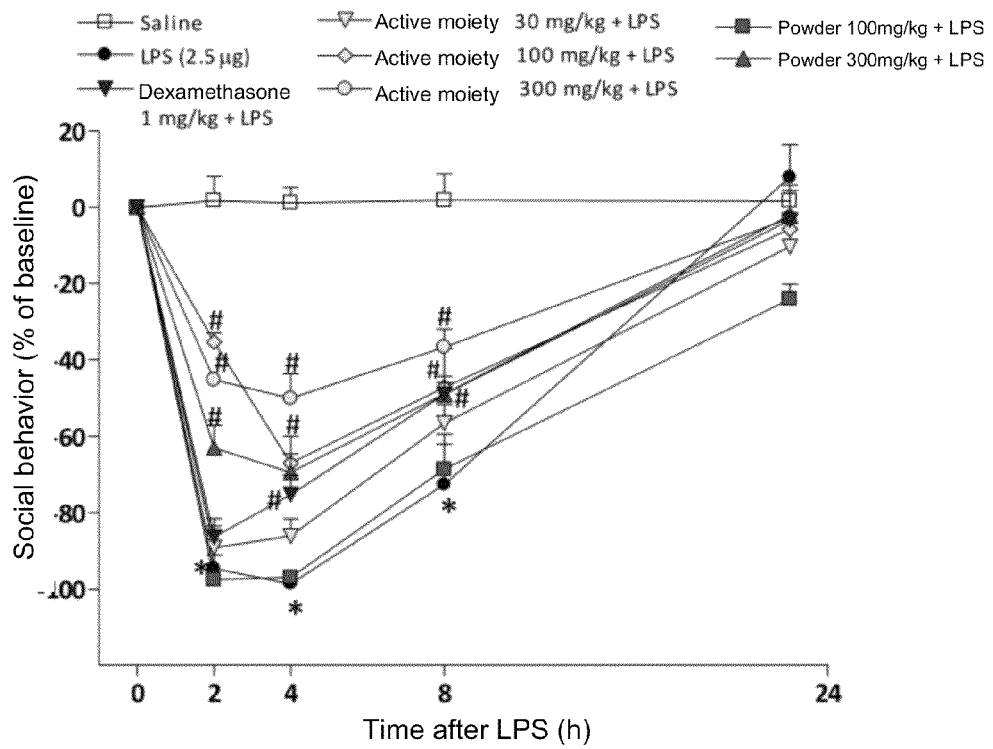
FIGS. 1A to 1D compare the effect of the active moiety according to the present invention and a guarana powder available on the market (in the graphs, powder refers to guarana powder available on the market). The effect of pretreatment with saline, vehicle, dexamethasone (1 mg/Kg, s.c.), active moiety (30-300 mg/Kg, p.o.) or powder (100 and 300 mg/Kg, p.o.) can be verified in the social behavior FIGS. 1A to 1D compare the effect of the active moiety according to the present invention and a guarana powder available on the market (in the graphs, powder refers to guarana powder available on the market). The effect of pretreatment with saline, vehicle, dexamethasone (1 mg/Kg, s.c.), active moiety (30-300 mg/Kg, p.o.) or powder (100 and 300 mg/Kg, p.o.) can be verified in the social behavior (FIG. 1A), evaluated (0, 2, 4, 8 and 24 h) after the administration of lipopolysaccharide (LPS) and the corresponding area under the curve (FIG. 1B). As it can be verified, open field (FIG. 1c) was also assessed 2 h after administration of LPS. Food intake (FIG. 1D) was evaluated 24 h after administration of LPS. Columns represent the average of 6-8 animals per group and vertical bars represent the standard deviation from the mean. * $p<0.05$, in comparison with saline (control); # $p<0.05$ in comparison with the vehicle.

The present invention relates to an active moiety of *Paullinia cupana* that is effective against fatigue, particularly related to cancers. Said active moiety contains an average content of theobromine ranging from about 0.05 to about 1% by weight, particularly about 0.1% by weight, and particularly about 10 to about 20% by weight of caffeine.

According to the present invention, "active moiety" means any fractions obtained from *Paullinia cupana*, containing the average contents of the compounds as described above, particularly of *Paullinia cupana* seed powder, according to the process described in this specification.

"Theobromine" means the compound named 3,7-dimethylxanthine or 3,7-dihydro-3,7-dimethyl-1H-purine-2,6-dione, also known as xantheose, with CAS registry number 83-67-0 (Chemical Abstract Service), and its derivatives.

"Caffeine" means the compound named 1,3,7-trimethylxanthine, with CAS registry number 58-08-2, and its derivatives.

"Guarana powder", which is used as a comparison parameter in the tests presented in this specification, and as starting material in the process according to the present invention, means the powder obtained by conventional process, which includes grinding of *Paullinia cupana* seeds, that have been previously roasted and peeled, as it is mentioned in the publication of Oliveira Júnior et al: *projeto potencialidades regionals, estudo de viabilidade econômica, guaraná*, Instituto Superior de Administração e Economia ISAE/Fundação Getúlio Vargas (FGV), 2003, incorporated herein by reference.

"Fatigue" means a set of symptoms clinically verified that significantly alter the overall capacity of the patient, which may have multiple origins, whose genesis and expression involve physical and psychic aspects (see publication of Giglio et al.: *Fadiga relacionada ao câncer*, Algoritmos, Einstein: Educ Contin Saúde. 2010; 8 (1 Pt 2): 44, incorporated herein by reference). The terms asthenia, lethargy, exhaustion, weakness feeling, extreme tiredness and lack of motivation can be mentioned herein as fatigue synonyms.

"Efficacy of treatment" means that the general state of the patient is restored, so that a noticeable improvement in the performance of physical and mental functions is presented, such as in social interaction, locomotor activity and food intake.

"Average content" means the amount of marker compound in relation to the total mass of the active moiety.

The active moiety, according to the present invention, is prepared from guarana powder. Hence, in a second aspect, the present invention is related to the process for producing an active moiety from guarana powder, comprising:

A) Extracting guarana powder, particularly in a shaker, with a mixture of lower alcohol ($C_1$ to $C_3$) and water, particularly in a ratio of about 70:30, during about 0.5 to 2 h, in which the ratio of powder:mixture is about 1:2 (Kg/L);

B) Filtering the product of the previous step, obtaining a first intermediate fraction;

C) The residue from filtration performed in step B is again submitted to extraction and filtering, under the same conditions, obtaining the second intermediate fraction.

D) The intermediate B and C fractions are mixed and dried, particularly in a rotary evaporator, obtaining the active moiety according to the present invention.

The active moiety of *Paullinia cupana* can be provided to the patient in a pure form, or with a carrier in appropriate dosage forms. Thus, the present invention is also related to pharmaceutical compositions containing the active moiety, according to the present invention or drugs containing the same.

The pharmaceutical compositions according to the present invention can be liquid, solid or semi-solid, and can be adapted to any enteral or parenteral route of administration, with immediate release or modified. In a particular embodiment, said pharmaceutical composition is adapted for oral administration, particularly as tablets or capsules.

The suitable pharmaceutically acceptable excipients, according to the present invention, are, for example and without limitation, those cited in Remington's Pharmaceutical Sciences, Mack Publishing, American or European Pharmacopoeia or Brazilian Pharmacopoeia.

Another object of the present invention relates to the use of the active moiety, according to the present invention, in the preparation of a drug useful for treating fatigue, particularly related to cancer.

The present invention further relates to a method for treating fatigue, particularly related to cancer, which consists in providing the active moiety, according to the present invention, to a patient in need thereof.

The present invention is further illustrated by the following examples, without limitation.

EXAMPLE 1

Preparation of the Active Moiety of *Paullinia cupana*

An amount of the active fraction according to the present invention was prepared using 2 Kg of guarana powder (batch number: PGUR0062F).

Guarana powder was submitted to extraction, in a mechanical stirrer, with 4 liters of a mixture of ethanol and water, in a ratio of 70:30, during 1 h at maximum speed.

Then, the product obtained was filtered in a Büchner funnel, obtaining the first intermediate fraction.

The filtration residue was then subjected to extraction with 2 liters of ethanol and water, in a ratio of 70:30, during 1 h at maximum speed. The product obtained was also filtered in a Büchner funnel, obtaining the second intermediate fraction.

The two intermediate fractions were mixed and dried in a rotary evaporator, obtaining about 500 grams of the active moiety according to the present invention.

EXAMPLE 2

Quantification of Theobromine and Caffeine Contents 500 grams of the active moiety according to the present invention were subjected to HPLC (High-performance liquid chromatography) for determining the contents of theobromine and caffeine.

The calibration curve was prepared weighing about 10 mg of analytical standards of theobromine and caffeine in 25 mL volumetric flasks and making up with mobile phase. From these stock solutions, serial dilutions were made to obtain the standard calibration curve, filtering with 0.45 μm membrane and injecting in the chromatograph.

The samples were prepared by analytically weighing about 50 mg of the sample in 25 mL volumetric flasks and making up with mobile phase, filtering with 0.45 μm membrane and injecting into the chromatograph.

The chromatographic conditions for theobromine analysis were:

Waters Alliance LC-DAD System consisting of a 2695 pump, oven for column heating, 2996 diode array detector and Empower® software (Empower Software Solutions, Inc, US).
Column: Atlantis dC-18 100×2.1 mm, 3 μm with pre (35° C.)
Eluent: 0.1% formic acid/methanol (95/5 v/v)
Flow rate: 0.25 mL/min
Detection at 273 nm
Injected Volume: 20 μL The chromatographic conditions for caffeine analysis were:

Waters Alliance LC-DAD System consisting of a 2695 pump, oven for column heating, 2996 diode array detector and Empower® software.
Column: NOVA PAK CN HP (150×3.9×4 μm) (30 ° C.)
Eluent: 2 mM phosphoric acid/methanol (95/5 v/v)
Flow rate: 0.8 mL/min
Detection at 273 nm
Injected Volume: 10 μL.

The average content of theobromine in the sample of active moiety, according to the present invention, was 0.096% and the average content of caffeine was 16.16%.

EXAMPLE 3

Efficacy Tests

Materials and Methods

Animals

Female SPF (Specific Pathogen Free)BALB/c mice were used, weighing between 20-25 g. The animals were kept in individual cages with ventilation, under sterile conditions (free of pathogens), with controlled temperature (22±1° C.) and humidity (60-80%) in 12 hours of light/dark cycle, with access to water and feed ad libitum.

Behavior of the Disease

The mice were subjected to two behavioral tests: one evaluates the interaction and social relationship (Fishikin et al.: *Endotoxin-induced reduction of social investigation by mice: interaction with amphetamine and anti-inflammatory drugs*. Psychopharmacology (Berl) 132, 335-341, 1997), while the other model evaluates the locomotor activity (Dunn et al.: *Effects of inteukin-1 and endotoxin in the forced swim and tail suspension tests in mice*. Pharmacology Biochemistry and Behavior 81, 688-693, 2005). Additionally, food intake was monitored during 24 h.

Social Interaction, Locomotor Activity and Food Intake

The animals were divided into eight experimental groups. Control groups orally received saline or vehicle (p.o.). One group was treated with dexamethasone subcutaneously (DEX; 1 mg/Kg, s.c.). Three groups were treated with the active moiety according to the present invention (30-300 mg/Kg, p.o.) and two groups were treated with guarana powder (100 and 300 mg/Kg, p.o.).

Saline was administered in the negative control group 1 hl after treatment. 100 μL of lipopolysaccharide were administered to the other groups (LPS; 2.5 μg/mouse, i.p.) 1 h after the respective treatments.

The evaluations were carried out taking into account three criteria: interaction in social relationships, being held after introducing a young mouse during 5 minutes in the box with a test mouse. Evaluations were carried out immediately before and after administration of LPS or saline (0, 2, 4, 8 and 24 h). Another behavioral assessing criterion was food intake monitoring, which was performed by weighing after 24 h of LPS intake. Finally, in order to verify locomotor changes, mice were submitted to 6-minute open field test after 2 h of LPS administration. The apparatus consisted of a box with arena floor divided into 12 equal squares. During the experiment, each mouse was placed in the middle of the open field. The number of intersections with all legs were recorded and taken as locomotor activity index.

Cytokine Dosage

The levels of IL-1β and IL-6 were evaluated as previously described (Ferreira et al: *the use of kinin B1 and B2 receptor knockout mice and selective antagonists to characterize the nocieptive responses caused by kinins at the spinal level*. Neuropharmacology 43, 1188-1197, 2002), with few modifications. The blood and brain were collected 2 h after administration of LPS (2.5 μg/mouse i.p.). Blood was collected with heparin (50 IU/mL) and immediately centrifuged at 10,000 rpm during 15 minutes. Plasma was removed and stored at −70 ° C. for future analysis of cytokines. The brains were removed and homogenized with PBS containing Tween 20 (0.05%), 0.1 mM phenylmethylsulfonyl fluoride, 0.1 mM benzethonium chloride, 10 mM EDTA, and 2 ng/mL of aprotinin. The solution formed was centrifuged at 3,000×g for 10 minutes at 4° C., and the supernatant was stored at −70° C. The cytokine levels were determined using specific ELISA kits (Enzyme Linked Immunosorbent Assay, R&D systems, US) according to the manufacturer's recommendations.

Reverse Transcription Followed by Polymerase Chain Reaction in Real Time (Real Time-RT-PCR)

In order to determine changes in the expression of messenger RNA (mRNA) of cytokines IL-12, IL-6, TNF-α and INF-γ, brain was collected 2 h after administration of LPS (2.5 μg/mouse, i.p.) and subjected to RT-PCR. mRNA was extracted from the brain, quantified and the corresponding sequences of IL-12, IL-6, TNF-α and INF-γ were amplified with specific oligonuceotides. The samples were homogenized in trizol according to manufacturer recommendations.

For the reverse transcription reaction, enzyme Moloney Murine Leukemia Virus (M-MLV) was used (Invitrogen, US).

Samples containing 2 μg of total RNA were incubated in a final reaction volume of 20 μL, according to manufacturer recommendations.

For obtaining complementary DNA, the mixture was subjected to a temperature of 20° C. for 10 min, 42° C. for 45 min and 95° C. for 5 min.

The Real Time PCR detection system iCycle iQ (Bio-Rad, US) was used to obtain the cDNA amplification data in real time.

For PCR reaction, the kit Master Mix TaqMan and TaqMan Gene Expression (Applied Biosystems, US) was used.

GAPDH of each sample was simultaneously amplified for further standardization of results. The fluorescence was recorded at the end of each extension phase (72° C.). Data generated by the fluorophore of TaqMan probe were analyzed and the calculation of cDNA amplification for IL-6, IL-12, TNF-α and INF-γ were normalized using GAPDH.

Statistical Analysis

All data are expressed as mean±standard deviation from the mean. The statistical difference was measured by one-way ANOVA followed by the Student Newman-Keuls test, and for two-way, Bonferroni test was used. The statistical analyses were performed using Graphpad Prism 4 software (GraphPad Software Inc., San Diego, USA).

Results

Active Moiety, According to the Present Invention, and Guarana Powder Protects from LPS-Induced Social and Locomotor Deficit The first objective of this study was to verify if the treatment with different doses of active moiety, according to the present invention, or guarana powder, would protect from LPS-induced social integration and locomotor damage. For this, social interaction, locomotor activity and food intake tests were performed in all experimental groups. Animals receiving vehicle+LPS showed prejudice on social interaction in a time-dependent manner (FIG. 1A), also observed in the area under the curve (FIG. 1B), as well as a significant reduction in the number of open field crossings (FIG. 1C). Additionally, there was a significant reduction in food intake in the vehicle+LPS group (FIG. 1D).

Figure 1B:
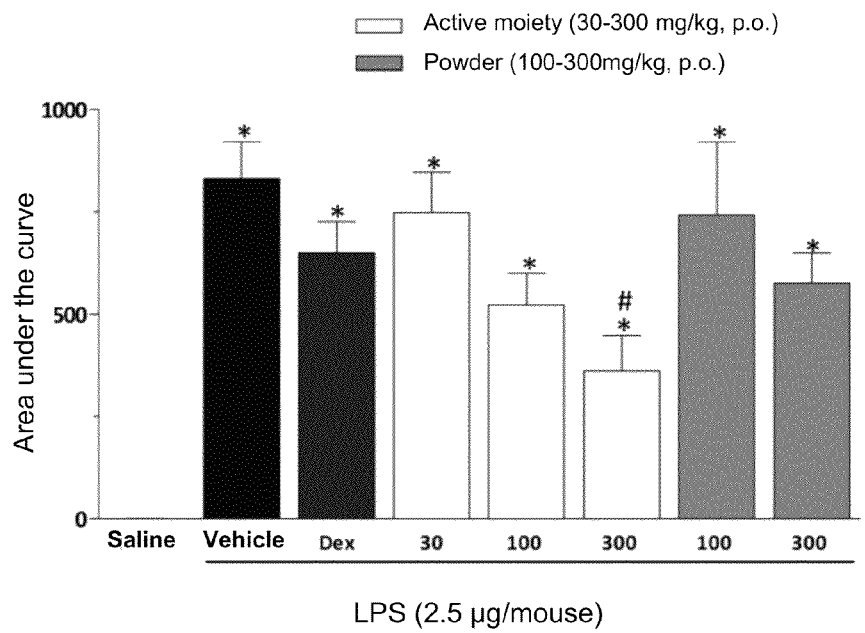
Figure 1C:
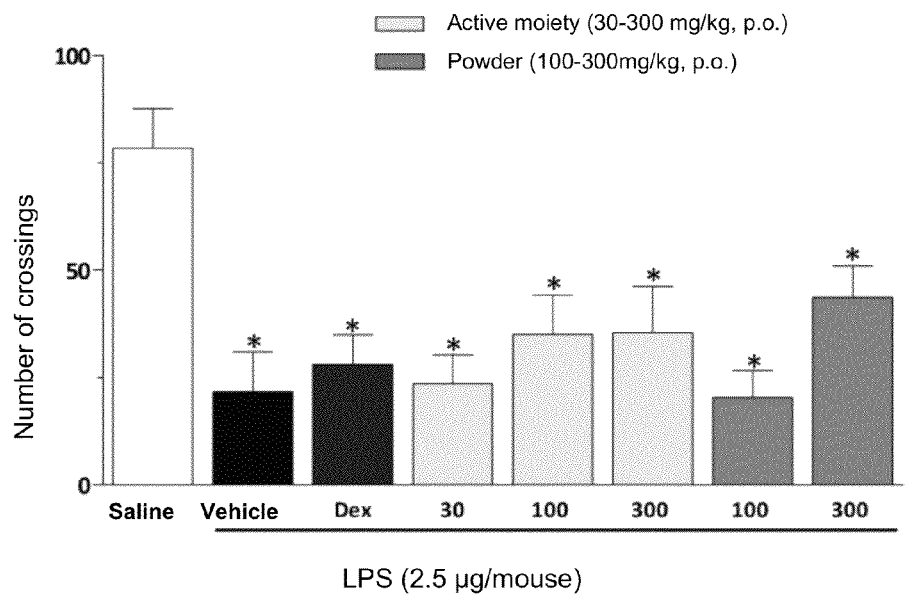
Figure 1D:
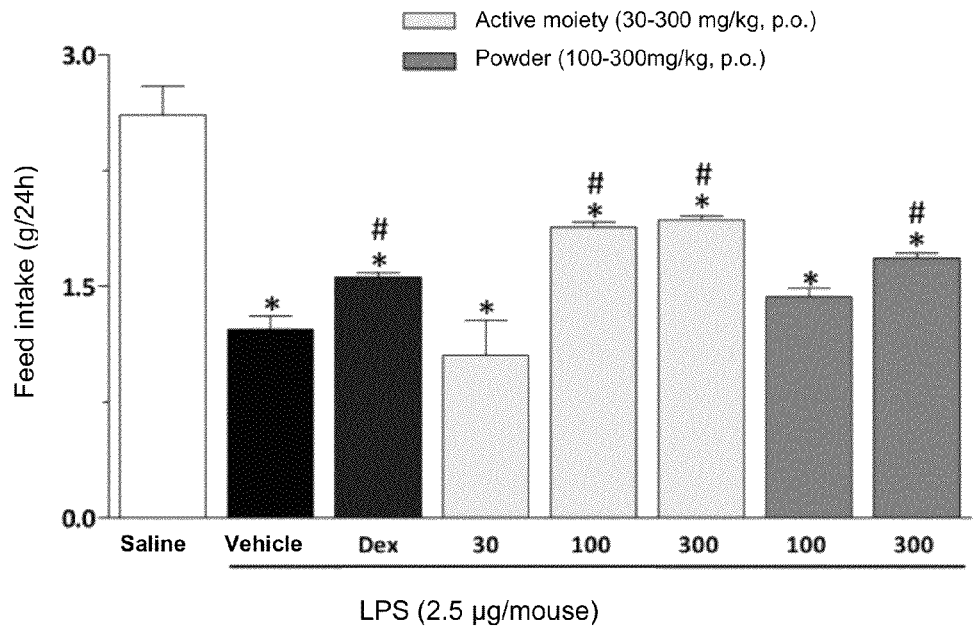

Treatment with the active fraction according to the present invention was able to increase social interaction and food intake in a dose-dependent manner, with significant improvement in both 100 mg/Kg and 300 mg/Kg (FIGS. 1A, B and D).

The treatment with guarana powder partially improved social interaction and food intake, this effect being observed only at a dose of 300 mg/Kg (FIGS. 1A, B and D). The control dexamethasone was able to partially protect social integration damage induced by LPS (FIGS. 1A and B), as well as increased feed intake (FIG. 1D).

The active moiety according to the present invention and guarana powder modulate cerebral IL-1β, but do not alter the levels of LPS-induced circulating IL-6.

In a complementary manner, since LPS reduce social interaction and the treatment with active moiety in accordance with the present invention and guarana powder significantly improves this parameter, the role of IL-6 and IL-1β cytokines related to this effect was investigated.

For this purpose, plasma levels of IL-6 and cerebral IL-1β in saline, vehicle and dexamethasone groups (1 mg/Kg, s.c.), the active moiety according to the present invention (100 mg/Kg, p.o.) or guarana powder (300 mg/Kg, p.o.) 2 h after administration of LPS in mice (FIGS. 2A and B) were analyzed.

Figure 2A:
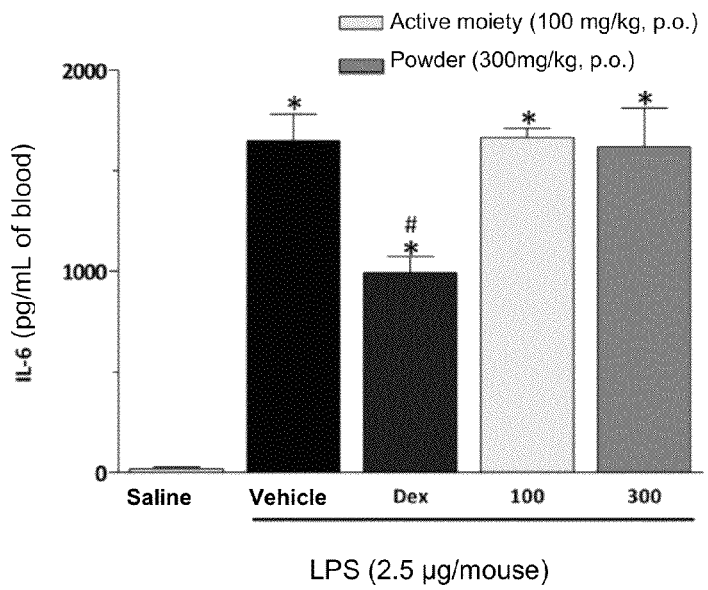
FIGS. 2A and 2B show comparisons between the effect of active moiety according to the present invention and guarana powder on the market, in relation to the circulating levels of IL-6 and cerebral IL-1β (in the graphics, powder refers to conventional guarana powder). The effect of pretreatment with saline, vehicle, dexamethasone (1 mg/Kg, s.c.), active moiety (100 mg/Kg, p.o.) or powder (300 mg/Kg, p.o.) in IL-6 plasma levels (FIG. 2A) and cerebral IL-1β (FIG. 2B) 2 h after administration of lipopolysaccharide (LPS) is verified. The columns represent the average of 6-8 animals per group and the vertical bars represent the standard deviation from the mean. * $p<0.05$, in comparison with saline (control); # $p<0.05$ in comparison with the vehicle.
Figure 2B:
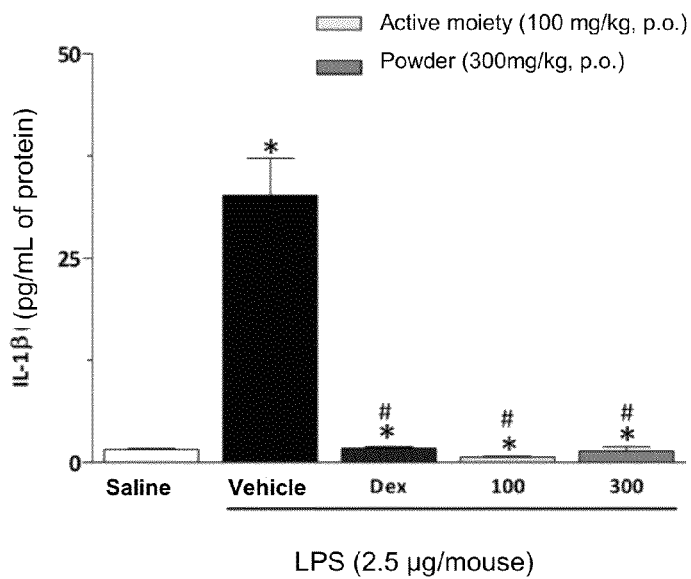

IL-6 plasma levels were significantly increased in the groups receiving LPS, in relation to the saline group. The treatments with active moiety according to the present invention and with guarana powder did not protect from IL-6 increase in plasma levels; however, control dexamethasone significantly reduced IL-6, compared with the vehicle group (FIG. 2A). It was observed that LPS was able to increase cerebral levels of IL-1β (FIG. 2B). Total protection in cerebral IL-1β levels in animals treated with the active moiety, according to the present invention, guarana powder and dexamethasone (FIG. 2B) was observed.

Active Moiety in Accordance with this Modulates the Expression of LPS-Induced Pro-Inflammatory Cytokines It is known that pro-Inflammatory cytokines produced and released into the brain are directly related to the behavior of diseases, and therefore, it has an effect on locomotion and food intake. Therefore, the expression of pro-inflammatory mediators was investigated in the brain.

For this purpose, the expression of IL-12, IL-6, TNF-α and INF-γ cytokines 2 h after administration of LPS was evaluated. It was observed that LPS induces expression of these cytokines in the brain, which could explain the fact that animals treated with vehicle and subsequently with LPS exhibited locomotor impairment, reduced social interaction and low food intake.

Figure 3A:
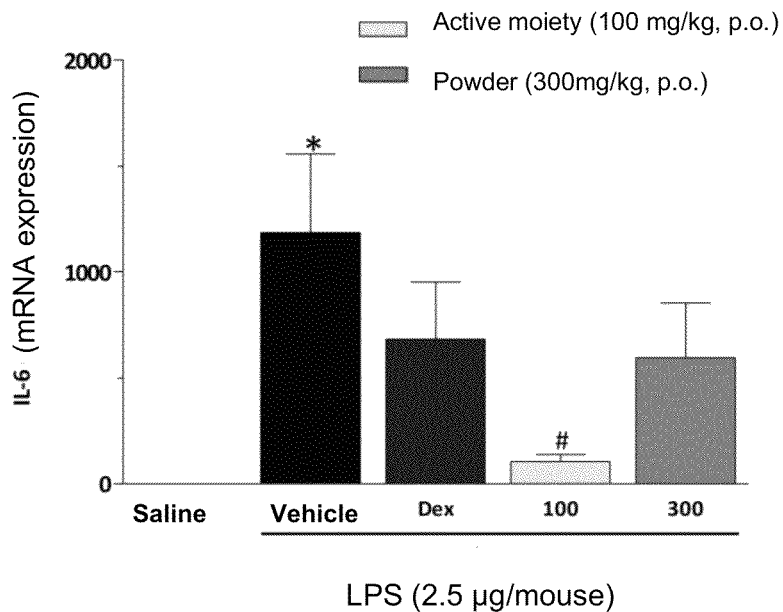
FIGS. 3A to 3D present comparisons between the effect of the active moiety according to the present invention and guarana powder found on the market on the expression of pro-inflammatory cytokines in the brain (in the graphics, powder refers to guarana powder available on the market). The effect of pretreatment with saline, vehicle, dexamethasone (1 mg/Kg, s.c.), active moiety (100 mg/Kg, p.o.) or powder (300 mg/Kg, p.o.) on messenger RNA expression of cytokines IL-6 (FIG. 3A), TNF-α (FIG. 3B), IL-12 (FIG. 3c) and INF-γ (FIG. 3D) is verified, 2 h after administration of lipopolysaccharide (LPS). Columns represent the average of 6-8 animals per group and vertical bars represent the standard deviation from the mean. * $p<0.05$, in comparison with saline (control); # $p<0.05$ in comparison with the vehicle.
Figure 3B:
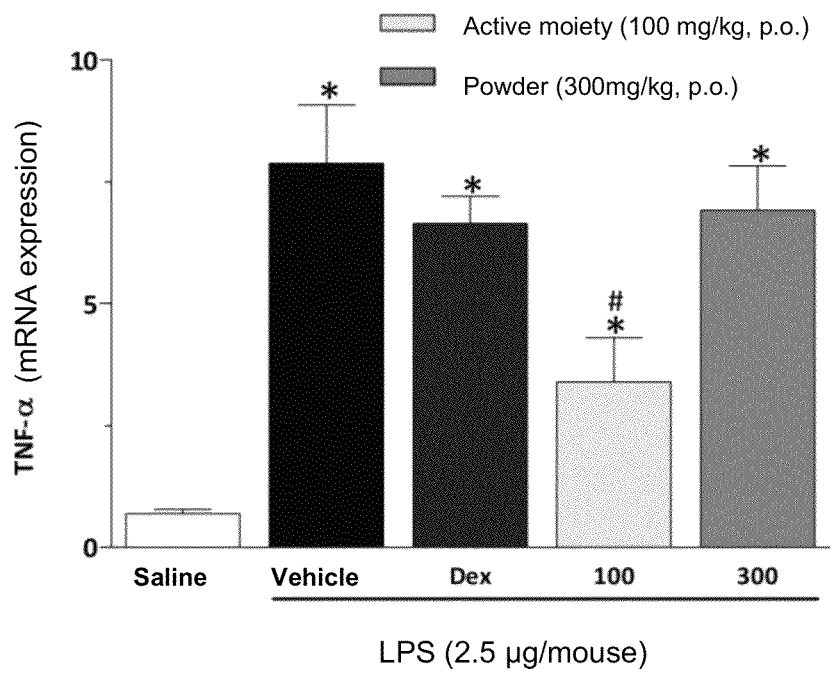
Figure 3C:
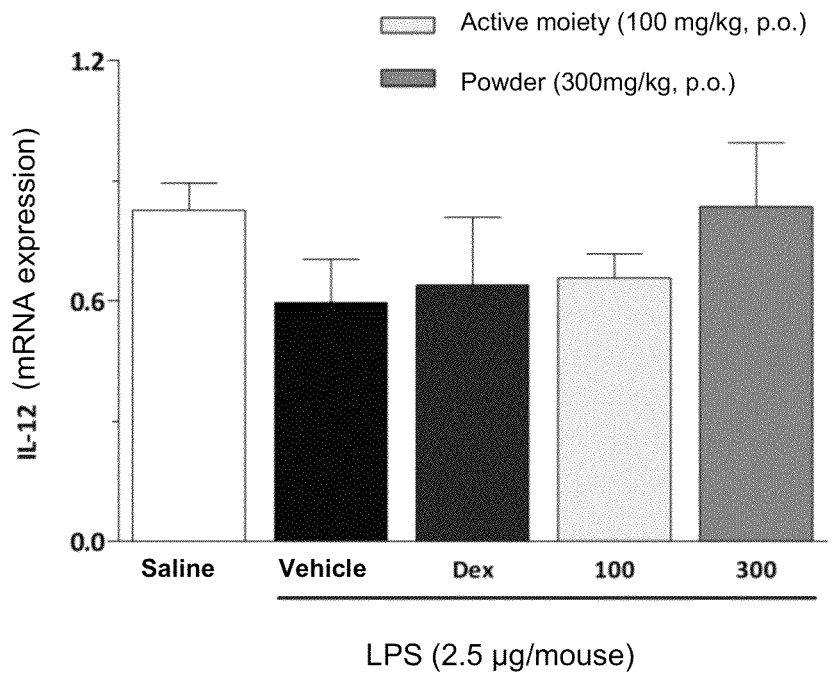
Figure 3D:
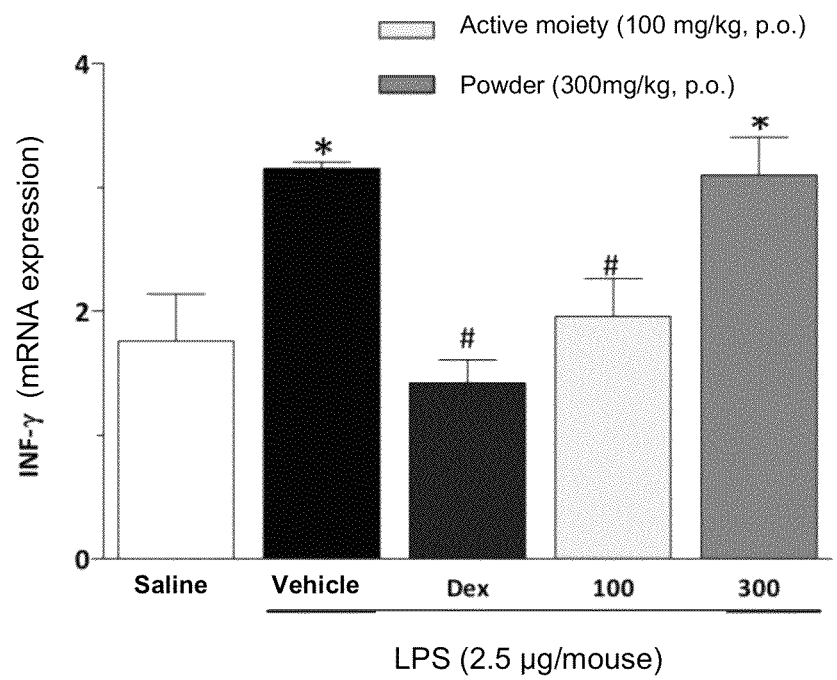

Treatment with the active moiety, according to the present invention (100 mg/Kg, p.o.), was able to significantly reduce the expression of IL-6, TNF-α, INF-γ (FIGS. 3A, B and D). The treatment with guarana powder (300 mg/Kg, p.o.) did not change mRNA levels of LPS-induced cytokines. Control dexamethasone significantly reduced mRNA levels of INF-γ (FIG. 3D). mRNA of IL-12 cytokine did not show significant difference between experimental groups.

EXAMPLE 4

Efficacy Tests in Humans

The study was conducted in order to evaluate the performance of active moiety according to the present invention in patients with different types of tumors, who receive different chemotherapy schemes.

Patients with solid tumors, over 18 years of age, who received systemic chemotherapy. Patients with fibromyalgia and uncontrolled hypothyroidism, depression, anemia, hypertension or heart disease were excluded.

Basal fatigue was evaluated with the use of a questionnaire prior to chemotherapy. Only patients that experienced a score increase after one week were included in the study.

The active moiety according to the present invention was provided after a week of chemotherapy (50 mg orally twice a day).

Questionnaires known in the art were used (FACIT-F, BFI, Chalder, HADS and PSQI) to evaluate fatigue, anxiety, depression and sleep quality in one week and after 4 weeks of chemotherapy. As a result, 36 patients were included in the study, with an average age of 54 years, being 61% female, of which 28% had with breast cancer, 22% had colorectal cancer, 8.3% had lung cancer, 8.3% had head/neck cancer, 5.6% had ovarian cancer and 27% had other carcinomas.

It was observed that fatigue scores significantly improved in comparison with the scores of BFI questionnaires (mean difference=19.39; 95% of CI 12.4-26.37, p<0.0001), FACIT-F (average difference=−11.51; 95% of CI−19.25-3.76, p=0.0049) and Chalder (mean difference=4.571; 95% of CI 1.86-7.28, p=0.0018).

Additionally, the scores of HADS subscales of anxiety (p=0.025) and depression (p=0.0095) also significantly improved after 3 weeks of therapy with the active moiety, according to the present invention. PSQI scores did not change significantly (p=0.26) after 3 weeks of treatment with the active moiety, according to the present invention.

Thus, studies have shown that the active moiety, according to the present invention, is effective for treating chemotherapy-related fatigue in patients with a multitude of solid tumors, and acts in anxiety and depression scores, without worsening sleep quality.

It shall be understood that the embodiments described above are merely illustrative and any modification to them may occur for a person skilled in the art. Therefore, the present invention should not be considered limited to the achievements described in the present application.

The person skilled in the art can readily evaluate, by means of the teachings contained in the text and in the presented examples, advantages of the invention, and propose modifications and equivalent alternatives to the embodiments, without departing from the scope of the invention, as defined in the attached claims.

The invention claimed is:

1. A method for treating cancer-related fatigue comprising administering to a patient 50 mg orally twice a day of an active moiety of *Paullinia cupana* comprising from 0.05 to 1% by weight of theobromine and from 10 to about 20% by weight of caffeine, wherein said moiety of *Paullinia cupana* is obtained from seed powder of *Paullinia cupana* by a method comprising the steps of:

(a) submitting 2 kg of Paullinia cupana seed powder to extraction, under agitation, with 4 liters of a mixture of ethanol and water, in a 70:30 ratio, for 1 h;

(b) filtering the product obtained in (a), the obtained filtrate being a first intermediate fraction;

(c) extracting the filtration residue of (b) with 2 liters of a mixture of ethanol and water, in a 70:30 ratio, for 1h under agitation;

(d) filtering the product obtained in (c), the obtained filtrate being a second intermediate fraction; and (e) mixing and drying the two intermediate fractions.

* * * * *